United States Patent [19]

Sakata et al.

[11] Patent Number: 5,470,751
[45] Date of Patent: Nov. 28, 1995

[54] REAGENT FOR DETECTING MALARIA INFECTED CELLS AND A DETECTING METHOD FOR MALARIA INFECTED CELLS USING THE SAME

[75] Inventors: Takashi Sakata, Kakogawa; Hideaki Matsumoto, Takasago, both of Japan

[73] Assignee: Toa Medical Electronics Co., Ltd., Hyogo, Japan

[21] Appl. No.: 199,339

[22] Filed: Feb. 18, 1994

[30] Foreign Application Priority Data

Feb. 22, 1993 [JP] Japan ................. 5-031757

[51] Int. Cl.⁶ ............................. G01N 33/48
[52] U.S. Cl. ................. 436/63; 436/18; 436/166; 436/811
[58] Field of Search ................. 436/8, 17, 63, 436/166, 800, 811

[56] References Cited

U.S. PATENT DOCUMENTS

| | | | |
|---|---|---|---|
| 4,971,917 | 11/1990 | Kuroda | 436/63 |
| 4,981,803 | 1/1991 | Kuroda | 436/63 |
| 4,985,171 | 1/1991 | Kuroda et al. | 252/408.1 |
| 4,985,174 | 1/1991 | Kuroda et al. | 252/408.1 |

FOREIGN PATENT DOCUMENTS

| | | |
|---|---|---|
| 61-280565 | 12/1986 | Japan . |
| 62-34058 | 2/1987 | Japan . |
| 64-35366 | 2/1989 | Japan . |
| 64-35367 | 2/1989 | Japan . |
| 2074340 | 10/1981 | United Kingdom . |

OTHER PUBLICATIONS

Database WPI, Section Ch, Week 8712, Derwent Publications Ltd., Reticulocyate Determination Using Flow . . . , Feb. 1987.
van Vianen et al., Cytometry, Flow Cytometric Screening of Blood . . . , vol. 14, pp. 276–280, 1993.
Pattanapanyasat et al., Cytometry, Two–Color Flow Cytometric Analysis . . . , vol. 14(4), pp. 449–454, 1993.
Rickman et al., The Lancet, Rapid Diagnosis of Malaria By . . . , vol. 1989, pp. 68–71, 1989.
Pattanapanyasat et al., Cytometry, Flow Cytometric Two–Color . . . , vol. 13, pp. 182–187, 1992.
Jacobberger et al., Cytometry, Analysis of Malaria Parasite–Infected . . . , vol. 4, pp. 228–237, 1983.
J. M. Whaun et al., Cytometry, Rapid Identification and Detection of . . . , vol. 4, No. 2, pp. 117–122, 1983.
M. T. Makler et al., Cytometry, Thiazole Orange: A New Dye . . . , vol. 8, pp. 568–570.
"Rinshokensa" vol. 23, No. 4.
"Rinshokensa" 32(7)—1988, pp. 803–806.

"Cytometry" 4:117–122 (1983).
"Cytometry" 8:568–570 (1987).
"Cytometry" 4:228–237 (1983).
"Cytometry" 13:182–187 (1992).

Primary Examiner—David A. Redding
Attorney, Agent, or Firm—Birch, Stewart, Kolasch & Birch

[57] ABSTRACT

A reagent for staining malaria infected cells and a method for detecting malaria infected cells using the same, wherein the regent is a staining solution comprising at least one first dye of an Auramine analogue having the formula (I):

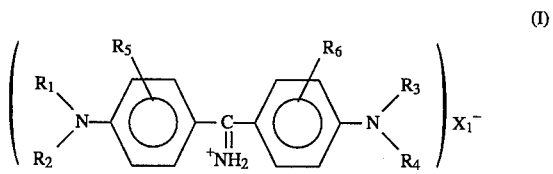

wherein $R_1$ to $R_6$ represents a hydrogen atom, or a methyl or ethyl group, $X_1$ represents a halogen atom, and at least one second dye of a condensed benzene derivative having the formula (II):

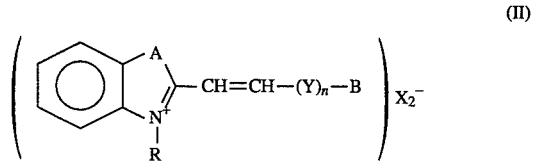

wherein A represents

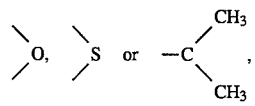

R represents a $C_{1-6}$ alkyl group, $X_2$ represents a halogen atom, Y represents —CH= or —NH—, n represents 0 or 1, and B represents

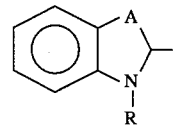

or a phenyl group substituted with 2 lower alkoxy group or with 1 di-lower alkylamino group. A test sample is treated with reagent to stain malaria infected cells. The stained malaria infected cells are then optically detected.

22 Claims, 4 Drawing Sheets

REAGENT FOR DETECTING MALARIA INFECTED CELLS AND A DETECTING METHOD FOR MALARIA INFECTED CELLS USING THE SAME

BACKGROUND OF THE INVENTION

1. Field of the Invention

The invention relates to a reagent for detecting malaria infected cells and a detecting method for malaria infected cells using the reagent by which malaria infected cells, in particular malaria infected erythrocytes, can be stained rapidly and specifically.

2. Description of the Related Art

When a living body is infected by malaria or Plasmodium, malaria enters into erythrocytes and grows. Detecting malaria infected erythrocytes is an effective method for examining the possibility of the malaria infection.

Conventional methods for detecting malaria infected erythrocytes are as follows.

In one known method, malaria infected erythrocytes are detected by staining a blood smear with Giemsa stain and observing it with a microscope (see, for example, Toshio Nakamura et al., "An Examination Method for Plasmodium", *Rinsho Kensa*, Vol. 23, No. 4: 335–341, 1979). Another known method is staining a blood smear with a fluorescent dye and then observing with a fluorescent microscope to detect malaria infected erythrocytes (see Humihiko Kawamoto, "Simple and Rapid Staining for Diagnosis of Protozoal Infection with Fluorechromes", *Rinsho Kensa*, Vol. 32, No. 7: 803–806, 1988).

However, these methods are troublesome due to the necessity of steps for preparing, drying, fixing, and staining a blood smear, and also need a skilled technique for distinguishing malaria infected erythrocytes from erythrocytes which are not infected. Further, the microscopic observation takes a long time (generally more than 15 minutes).

A method for detecting malaria infected erythrocytes by using a flow cytometry has been also developed. In this method, malaria infected erythrocytes are stained with a fluorescent dye and detected by a flow cytometry. The mechanism of this method is that Plasmodium is stained with a fluorescent dye and fluoresces upon irradiating by an argon laser, whereby malaria infected erythrocytes are detected. Various methods using the above mechanism are known as follows.

(1) J. W. Jacobberger, "Analysis of Plasmodium-Infected Blood by Flow Cytometry", *Cytometry*, Vol. 4: 228–237, 1983

In this method, malaria infected erythrocytes are detected by a flow cytometry, using 3,3'-dimethyloxacarbocyanine: DiOCl (3) as a fluorescent dye. FIG. 7 of this document shows that the distribution of reticulocytes (Immature RBC: imRBC) and malaria infected erythrocytes (pRBC, ppRBC) are overlapped. Further, FIG. 2 is a photograph showing that the reticulocytes (imRBC) and malaria infected erythrocytes (pRBC, ppRBC) fluoresces by staining with DiOCl (3).

(2) M. T. Makler et al., "Thiazole Orange: A New Dye for Plasmodium Species Analysis", *Cytometry*, Vol. 8: 568–570, 1987

In this method, malaria infected erythrocytes are detected by a flow cytometry, using thiazole orange as a fluorescent dye. There is a description on page 569 in the middle to the left that reticulocytes are stained as a background staining.

(3) J. M. Whaum et al., "Rapid Identification and Detection of Parasitized Human Red Cells by Automated Flow Cytometry", *Cytometry*, Vol. 4: 117–122, 1983

In this method, malaria infected erythrocytes are detected by a flow cytometry, using acridine orange as a fluorescent dye. Since malaria infected erythrocytes contain malarial DNA, green fluorescence is emitted, while red fluorescence is emitted from reticulocytes owing to RNA contained in reticulocytes. Thus, reticulocytes can be distinguished from erythrocytes.

(4) K. Pattanapanyasat et al., "Flow Cytometric Two-Color Staining Technique for Simultaneous Determination of Human Erythrocyte Membrane Antigen and Intracellular Malarial DNA", *Cytometry*, Vol. 13: 182–187, 1992

This method uses propidium iodide (PI: emitting red fluorescence) as a fluorescent dye and an antigen to an antibody DAF (decay-accelerating factor) contained in erythrocytes membrane and measures an amount of erythrocyte membrane antigen and malaria infected erythrocyte.

The methods (1) and (2) described above have a drawback that malaria infected erythrocytes can not be accurately measured when reticulocytes and malaria infected erythrocytes are present together. The methods (3) and (4) require two measurements, i.e., red fluorescence and green fluorescence. Further, according to the method (3), since acridine orange which is used as a fluorescent dye, attaches to the passage of flow cytometry and measuring cell, significant contamination of the passage and the cell occurs. In the method (4), as monoclonal antibody is used, it takes more than 30 minutes to react with erythrocytes. Thus, these conventional methods have respective defects.

In addition to the references described above, followings are known.

(5) Japanese Laid-Open Patent Application 61-280565 (1986), corresponding to U.S. Pat. No. 4,985,174.

(6) Japanese Laid-Open Patent Application 62-034058 (1987).

These references disclose that a solution containing Auramine O as a fluorescent dye is mixed with a blood sample to stain reticulocytes with the fluorescent dye. As shown in the following table, four examples are described in the above reference (5), and one example in (6).

TABLE

|  | (5) - 1 | (5) - 2 | (5) - 3 | (5) - 4 | (6) - 1 |
|---|---|---|---|---|---|
| Amount of Auramine O/ 1 liter solution | 1000 mg | 400 mg | 30 mg | 400 mg | 1000 mg |
| Solution: Blood (vol.) (Dilution ratio) | 5 ml: 10 µl | 5 ml: 10 µl | 5 ml: 10 µl | 2 ml: 10 µl | 10 ml: 10 µl |
| Amount of Auramine O/ 1 µl blood | 500 µg/µl | 200 µg/µl | 15 µg/µl | 80 µg/µl | 1000 µg/µl |
| pH | 7.2 | 8.0 | 9.0 | 8.0 | 7.2 |

TABLE-continued

|  | (5) - 1 | (5) - 2 | (5) - 3 | (5) - 4 | (6) - 1 |
| --- | --- | --- | --- | --- | --- |
| Incubation temperature | room temp. | room temp. | room temp. | room temp. | room temp. |
| Incubation time | 10 min. | 10 min. | 10 min. | 30 sec. | 30 sec. |
| fluorescence wave length for detecting | 520 nm or more | 580 nm or more | 540 nm or more | 520 nm or more | 520 nm or more |

However, as described hereinafter, the reticulocytes and malaria infected erythrocytes are stained in the same level under the condition above. As a result, it is not possible to detect only the malaria infected erythrocytes.

Thus, conventional methods for detecting malaria infected erythrocytes retain defects to be improved.

SUMMARY OF THE INVENTION

The present invention provides a method for detecting malaria infected erythrocytes which uses the combination of Auramine O or its analogues with certain second dyes, thereby selectively staining said erythrocytes and detecting them by an optical means in a short time, and also a reagent for staining said erythrocyte.

Particularly, a detecting method for malaria infected cells comprises the steps of:

(1) treating a test sample with a staining solution which comprises at least one first dye of an Auramine analogue having the formula (I):

(I)

wherein $R_1$ to $R_6$ independently represent a hydrogen atom, or a methyl or ethyl group, and $X_1$ represents a halogen atom; and at least one second dye of a condensed benzene derivative having the formula (II):

(II)

wherein A represents

R represents a $C_{1-6}$ alkyl group,
$X_2$ represents a halogen atom,
Y represents —CH= or —NH—,
n represents 0 or 1, and
B represents or a phenyl group substituted with two of a lower alkoxy group with a lower alkyl group and a cyanoalkylamino group or with one of a di-lower alkylamino group, to stain malaria infected cells; and (2) optically detecting stained malaria infected cells.

DETAILED DESCRIPTION OF THE INVENTION

A method for detecting malaria infected cells of the present invention comprises a treating step in which a test sample is treated with a staining solution containing fluorescent dyes, and a detecting step in which the stained malaria infected cells are optically detected.

The test sample used in the present invention includes a blood sample derived from a human or animal blood, which may contain malaria infected erythorocytes. The term malaria means any kind of Plasmodium including human malaria (typically, *Plasmodium falciparum*).

The staining solution of the present invention comprises at least one first dye of an Auramine analogue having the formula (I) described above and at least one second dye of a condensed benzene derivative having the formula (II) described above.

In the formula (I), the halogen atom represented by $X_1$ includes iodine atom, bromine atom and chlorine atom.

In the formula (II), the $C_{1-6}$ alkyl group represented by R is preferably a straight chain alkyl, for example, methyl, ethyl, n-propyl, n-butyl, n-pentyl and n-hexyl. The phenyl group substituted with two of a lower alkoxy group represented by B includes 2,6-dimethoxyphenyl and 2,6-diethoxyphenyl; and the phenyl group substituted with di-lower alkylamino group represented by B includes 4-dimethylaminophenyl, 4-(cyanoethylamino)phenyl and 4-diethylaminophenyl.

Preferred examples of the first dye having the formula (I) are as follows:

Auramine O (CI No. 41000)

Basic Yellow 37 (CI No. 41001)

Basic Yellow 3 (Auramine G; CI No. 41005)

Among them, Auramine O is most preferable.

Preferred examples of the condensed benzene derivatives having the formula (II) are as follows:

3,3,-diethyl-2,2'-oxacarbocyanine iodide

2-(p-dimethylaminosthryl)-3-ethylbenzothiazolium iodide

3,3,-dimethyl-2,2'-oxacarbocyanine iodide

3,3'-(di-n-propyl)-2,2'-oxacarbocyanine iodide

3,3'-(di-n-pentyl)-2,2'-oxacarbocyanine iodide

3,3'-(di-n-hexyl)-2,2'-oxacarbocyanine iodide

2-(p-dimethylaminostyryl)-3-methylbenzoxazolium iodide

2-(p-dimethylaminostyryl)-1,3,3-trimetyl-3H-indolium iodide

Basic Yellow 11

Basic Red 14

Among them, 3,3'-diethyl-2,2'-oxacarbocyanineiodide is most preferable.

The staining solution of the present invention can be prepared by dissolving the first dye and the second dye in a water soluble organic solvent.

Preferred examples of the organic solvents are a lower alkanol, a lower alkylene glycol or a lower alkylene glycol monolower alkyl ether; such as methanol, ethanol, n-propanol, ethylene glycol, diethylene glycol, triethylene glycol, ethylene glycol monomethylether, ethylene glycol monoethylether, ethylene glycol mono(n-butyl)ether, diethylene glycol monoethylether. More preferably, ethylene glycol, diethylene glycol and triethylene glycol can be used. Most preferably, ethylene glycol can be used in view of the effect on erythrocytes and viscosity. The advantage of using such organic solvents are to prevent hydrolysis of the first dye (e.g. Auramine O).

The concentration of the first dye contained in the staining solution ranges from 0.005 to 0.4 w/v %, and the concentration of the second dye solution ranges from 0.005 to 0.5 w/v %.

According to the present invention, it is preferable to treat the test sample with the staining solution at a temperature of 25° to 40° C. for 20 to 60 seconds, preferably for 30 to 40 seconds, in order to stain the malaria infected cells specifically.

In the treating step, a test solution is prepared by mixing the test sample and the staining solution. It is very important to prepare the test solution at an appropriate stain concentration. In particular, the first dye is preferably contained in the test solution in the range from 1 to 80 ppm, more preferably from 5 to 50 ppm, and the second dye is preferably contained in the test solution in the range from 1 to 100 ppm, more preferably 5 to 50 ppm.

In order to prepare the staining solution such that the first and second dyes exist at the above concentration in the test solution, the test sample may be diluted with a diluent before treating with the staining solution. Alternatively, the test sample, diluent and staining solution may be combined together at the same time.

The preferred dilution ratio of the test sample (blood) is from 4 to 1,000 times. As the diluent, phosphate buffer or citrate buffer having a pH of 4 to 9 can be used. For example, TRIS buffer (sodium propionate (9.5 g/liter), tris(hydroxymethyl)aminomethane (0.6 g/liter) and tricin (7.4 g/liter)) is preferably used. If the test sample is mixed with the staining solution having a higher concentration of the dyes than that described above and allow the mixture to stand, the organic solvent contained in the staining solution adversely affect erythrocytes, so that the erythrocytes in the test sample are lysed. In addition, when the staining solution is too dilute or too concentrate, the reaction time would be extended or the difference in signal intensity between the malaria infected erythrocytes and reticulocytes would be made vague.

In the detecting step, it is preferable to use an optical means, particularly flow cytometry for optically detecting malaria infected cells which are stained with a fluorescent dye of the formula (I). For example, a flow cytometry which can watch and photograph the test particles in the sample stream by using a sequential light source may be used. The light source for this cytometry may be an argon laser having an exitation wavelength of 488 nm. The object to be detected is forward scattered light (FSC), and fluorescence (FL) having the wavelength of 525 nm or more. In Working Examples of the present invention, an automatic reticulocyte measuring device R-2000 (TOA medical Electrics Co., Ltd.) was employed.

The mechanism of the detecting method of the present invention is considered as follows.

Reticulocytes are immature red blood cells and belong to RNA protein. Reticulocytes are stained by precipitating and coagulating RNA by e.g., Auramine O. Because of the precipitation and coagulation of RNA, if the concentration of staining is low, the staining step takes a long time. On the other hand, leucocytes and malaria infected erythrocytes can be stained in a short time without waiting for their precipitation and coagulation even when a diluted staining solution is used because they contain DNA and inclusions. However, if the concentration of Auramine O is made low, a membrane of mature erythrocyte is hardly stained. It is a drawback of obtaining a sufficient fluorescence intensity.

It has been known that 3,3'-diethyl-2,2'-oxacarbocyanineiodide (Trade Name NK-85, available from Nihon Photosensitive Pigment Research) can stain a membrane of corpuscle. Based on this property, NK-85 is added. Then it was found that the fluorescence intensity can be enhanced generally and that sufficient difference in fluorescence intensity between the malaria infected erythrocytes and reticulocytes was unexpectedly detected. According to the present invention, it is the first dye of Auramine analogue that stains Plasmodium, so that DiOC2 (3) is not worked for staining Plasmodium.

The present invention is further described in detail with reference to a Reference Example and Working Examples as follows. However, it is not intended to limit the scope of the invention.

REFERENCE EXAMPLE 1

First, only Auramine O was used as a reagent for staining. Several staining solutions were prepared, varying the concentrations of the Auramine O. Then, a blood sample was measured by using a flow cytometry.

The composition of the staining solution and diluent used for this example was as follows:
<Stain Solution>
Auramine O (300–3,000 mg)
Ethylene glycol (100 ml)

The concentration of Auramine O ranges from 0.3 to 3.0%, and pH ranges from 3 to 9.5.
<Diluent>
Sodium propionate (9.5 g/l)
Tris(hydroxylmethyl)aminomethane (6.0 g/l)
Tricin (7.4 g/l)
<Test solution>
Blood Sample (10 µl)
Diluent (1950 µl)
Staining Solution (40 µl)

These three solutions in the amount mentioned above were mixed to prepare 2 ml of a test solution (the dilution ratio to the blood sample is 200). When preparing the test solution, the diluent was previously heated to 35° C. The mixture (test solution) was incubated for 30 minutes at 35° C., and introduced into a flow cell. Then, the forward scattered light (FSC) and fluorescence (FL) were measured for the respective cell groups.

Figure 1:
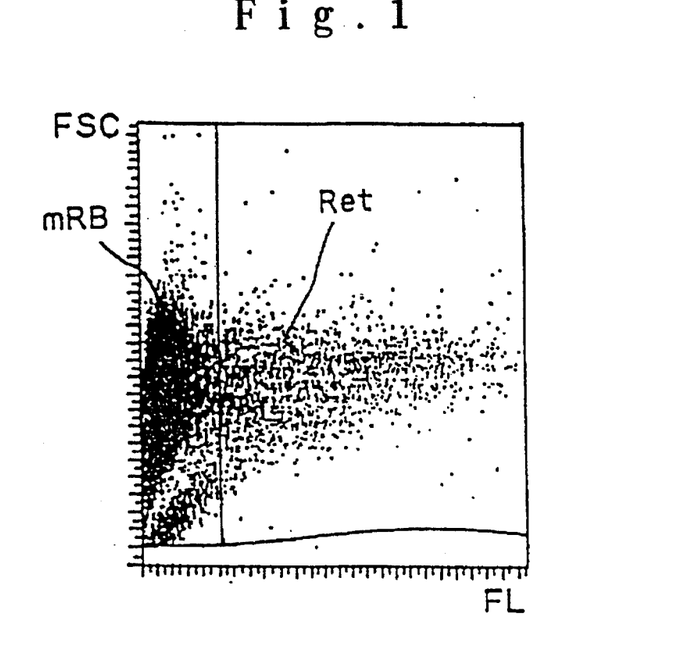
FIG. 1 shows a dimensional scattergram when a blood sample of hemoglobin H disease was measured by using a test solution containing 3.0% Auramine O staining solution for comparison.
Figure 2:
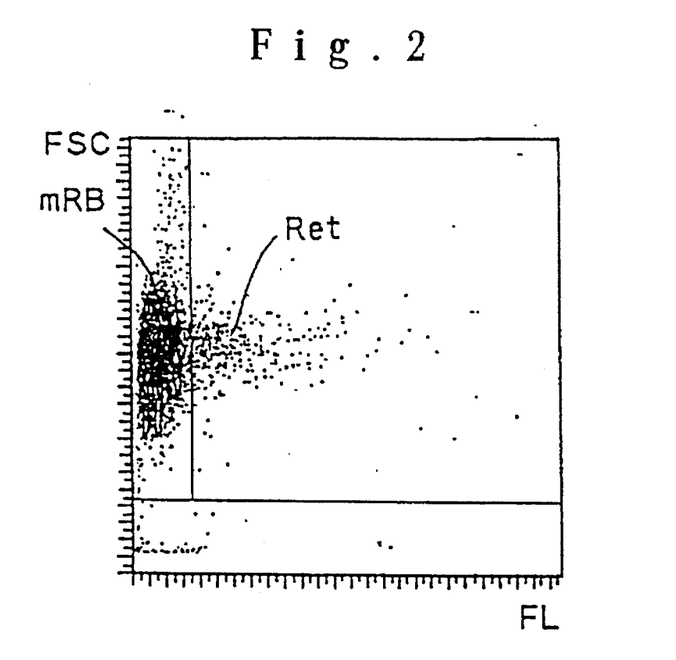
FIG. 2 shows a dimensional scattergram when a normal blood sample was measured by using a test solution containing 3.0% Auramine O staining solution for comparison.
Figure 3:
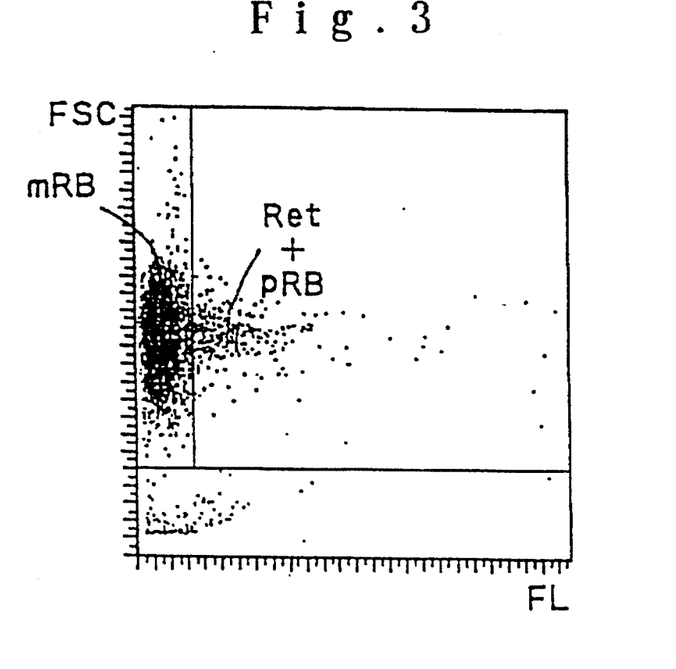
FIG. 3 shows a dimensional scattergram when a malaria infected blood sample was measured by using a test solution containing 3.0% Auramine O staining solution for comparison.

FIGS. 1 to 3 show the results of the measurement in case that the staining solution of 3.0% Auramine O was used (In this case, Auramine O was at 600 ppm in the test solution, and 120 µg per 1 µl of the blood sample).

In these figures, the result was obtained by a two dimension scattergram using a blood of hemoglobin H disease which contains a large amount of reticulocytes in FIG. 1; a normal blood which contains a few amount of reticulocytes and no malaria infected erythrocytes in FIG. 2; and a malaria infected sample which contains both of reticulocytes and malaria infected erythrocytes in FIG. 3. As seen from FIGS. 1 to 3, the reticulocytes (indicated by Ret in the figure) and malaria infected erythrocytes (indicated by pRB in the figure) appeared in the same region. Therefore, it is impossible to distinguish the reticulocytes from malaria infected erythrocytes. Incidentally, mRB shown in the figure refers to a mature erythrocyte.

Figure 4:
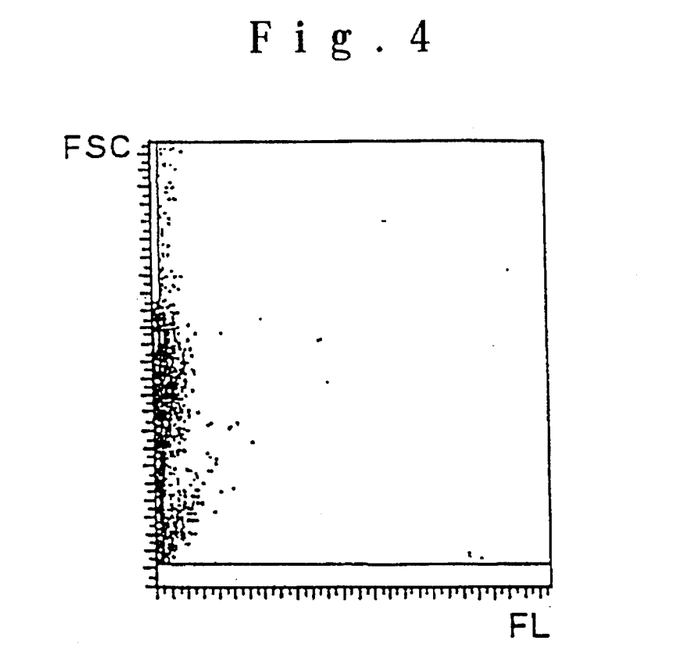
FIG. 4 shows a dimensional scattergram when a blood sample of hemoglobin H disease was measured by using a test solution containing 0.3% Auramine O staining solution for comparison.
Figure 5:
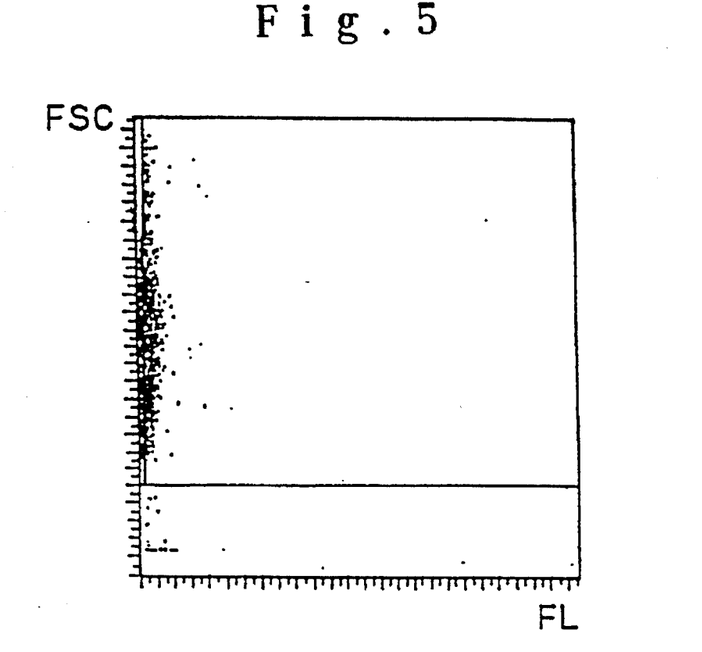
FIG. 5 shows a dimensional scattergram when a normal blood sample was measured by using a test solution containing 0.3% Auramine O staining solution for comparison.
Figure 6:
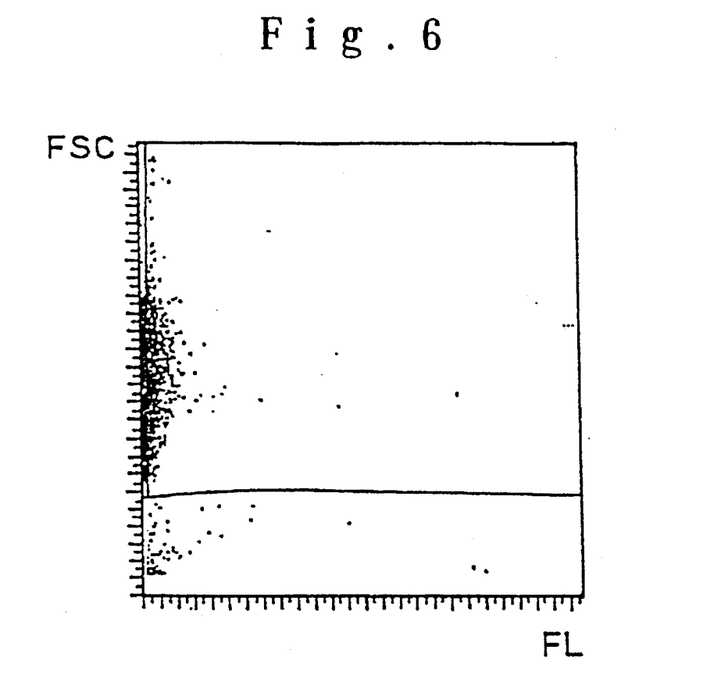
FIG. 6 shows a dimensional scattergram when a malaria infected blood sample was measured by using a test solution containing 0.3% Auramine O staining solution for comparison.

Next, the same sample was measured by using a staining solution containing Auramine O at a low concentration. FIGS. 4 to 6 show the result of measurement by using the same sample with a staining solution having a low concentration of Auramine O (i.e., 0.3% of Auramine O in the stain solution which corresponds to 60 ppm to the test solution and 12 µg of Auramine contained in 1 µl of the blood sample). FIGS. 4, 5 and 6 correspond to FIGS. 1, 2 and 3, respectively. The result that was obtained by using Auramine O at a concentration between 0.3 to 3.0% was not shown in the figures, but the detected area at the concentration was between the both areas.

According to the FIGS. 4 to 6, it was found that the difference occurs in fluorescence intensity between the reticulocytes and malaria infected erythrocytes. In other words, it was considered that there exists a certain condition that reticulocytes were not stained but malarial infected erythrocytes were stained.

However, as seen from FIGS. 4 to 6, the fluorescence intensity is weakened when simply reducing the concentration of Auramine O, and the difference in the fluorescence intensity is not necessarily generated. Therefore, examination was conducted by varying a measurement sensitivity, condition for incubation and the like. As a result, it was found that the fluorescence intensity was increased when the time for incubation is extended to 2 minutes, or when the reaction temperature is raised to 40° C.

However, the modification of such conditions was not considered to be sufficient for detecting the difference rapidly between the reticulocytes and malaria infected erythrocytes.

The present invention was achieved by studying the condition that a clear difference between the reticulocytes and malaria infected erythrocytes occurs stably in staining steps was conducted in about 30 seconds.

The problems above are dissolved by:
(a) reducing the concentration of Auramine O, and
(b) adding an additional dye.

WORKING EXAMPLE 1

A test solution was prepared as follows.

Auramine O (300 mg) and 3,3'-diethyl-2,2'-oxacarbocyanineiodide (50 mg) were dissolved in ethylene glycol (100 ml) to prepare a staining solution. The second dye, 3,3'-diethyl-2,2'-oxacarbocyanineiodide, was obtained from Nihon Photosensitive Pigment Research Co. as a trade name of NK-85. The concentration of Auramine O in this example was 0.3%, and that of 3,3'-diethyl-2,2'-oxacarbocyanineiodide (the second dye) is 0.005%.

The test solution and condition used for this example were the same as that of the Reference Example except for adding the second dye to the staining solution.

Figure 7:
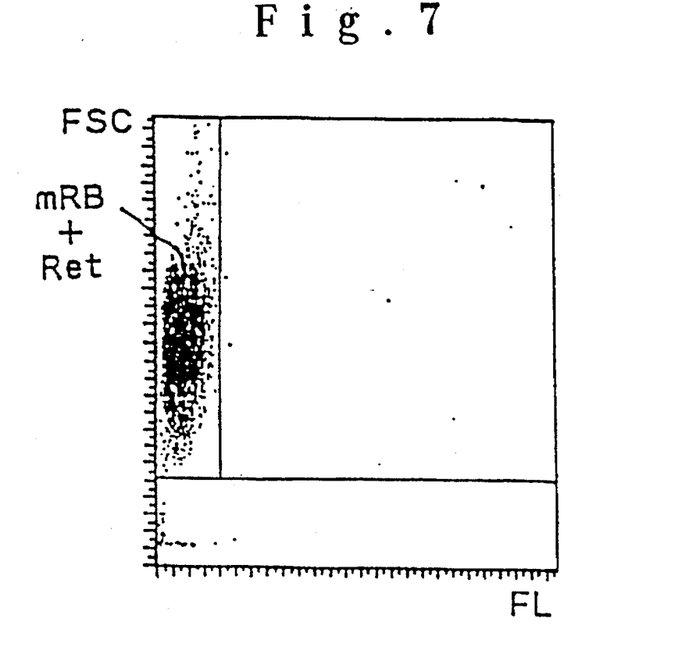
FIG. 7 shows a dimensional scattergram when a normal blood sample was measured by using a test solution described in Working Example 1 of the present invention.
Figure 8:
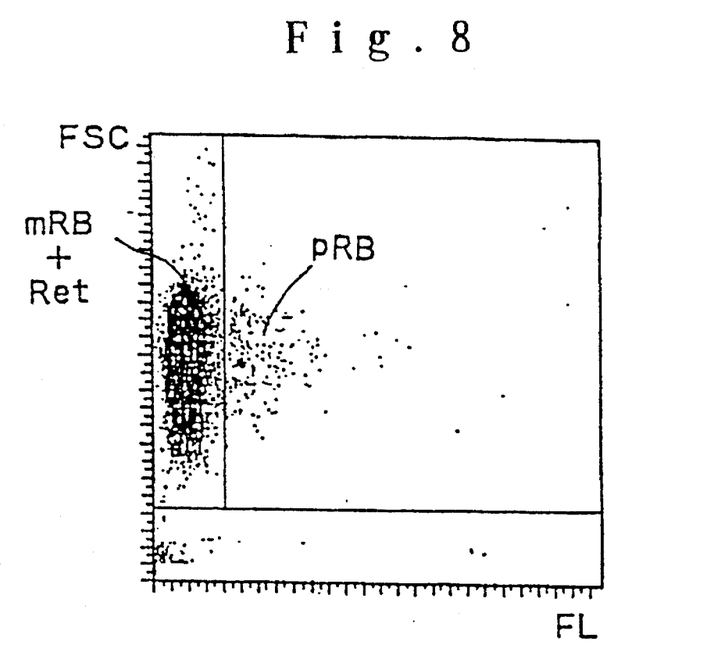
FIG. 8 shows a dimensional scattergram when a malaria infected blood sample was measured by using a test solution described in Working Example 1 of the present invention.

FIGS. 7 and 8 show the result when a normal test sample and malaria infected sample are used, which correspond to FIGS. 2 and 3, respectively. As is clearly seen from the comparison between these figures, only malaria infected erythrocytes pRB was stained well by fluorescence, thereby distinguishing matured erythrocytes mRB from reticulocytes Ret. Thus, the malaria infected erythrocytes pRB can be classified and counted. Although it is not described in the figures, leucocytes can be clearly distinguished from the erythrocytes because they are detected in the region where the fluorescence is strong.

WORKING EXAMPLE 2

This example was conducted similar to the Working Example 1 except that 2-(p-dimethylaminostyryl)-3-ethylbenzothiazoliumiodide (trade name: NK-91) was used instead of using 3,3'-diethyl-2,2'-oxacarbocyanineiodide. Then, the malaria infected erythrocytes were classified and counted.

In addition, tests were conducted by using a variety of second dyes that were also available for detecting malaria infected erythrocytes. As for the concentration, the final concentration to the test solution ranged from 1 to 100 ppm and the optimum concentration was from 5 to 50 ppm. The test conditions except for the concentration were the same as the case of using 3,3'-diethyl-2,2'-oxacarbocyanineiodide described above.

According to the reagent and detecting method of the present invention, malaria infected cells can be stained rapidly and specifically, thereby enabling them to be detected by a simple method. The effect of the present invention is extremely advantageous in the field of medical diagnosis.

What we claimed is:

1. A method for detecting malaria infected cells which comprises the steps of:
   (1) treating a test sample with a staining solution which comprises
       at least one first dye of an Auramine analogue having the formula (I):

(I)

wherein $R_1$ to $R_6$ independently represents a hydrogen atom, a methyl group or an ethyl group, and $X_1$ represents a halogen atom, and at least one second dye of a condensed benzene derivative having the formula (II):

(II)

wherein A represents

R represents a $C_{1-6}$ alkyl group,
$X_2$ represents a halogen atom,
Y represents —CH= or —NH—,
n represents 0 or 1, and
B represents or a phenyl group substituted with (i) two lower alkoxy groups, (ii) a lower alkyl group and a cyanoalkylamino group or (iii) one di-lower alkyamino group, to stain malaria infected cells; and (2) optically detecting stained malaria infected cells.

2. The method as in claim 1, wherein the first dye is Auramine O.

3. The method as in claim 1, wherein the second dye is 3,3'-diethyl-2,2'-oxacarbocyanine iodide.

4. The method as in claim 1, wherein the second dye is 3,3'-dimethyl-2,2a'-oxacarbocyanine iodide.

5. The method as in claim 1, further comprising diluting the test sample with a diluent having a pH of 4 to 9 prior to the treatment of step (1).

6. The method as in claim 1, further comprising diluting the test sample with a diluent having a pH of 4 to 9 simultaneously with the treating of the test sample with the staining solution.

7. The method as in claim 5, wherein the dilution ratio of the test sample is 4 to 1000 times.

8. The method as in claim 5, wherein the diluent is a solution comprising sodium propionate, tris(hydroxylmethyl)-aminomethane or tricin.

9. The method as in claim 1, wherein said test sample is treated in the step (1) such that the first dye and the second dye exist at a concentration of 1 to 80 ppm and 1 to 100 ppm, respectively.

10. The method as in claim 1, wherein step (1) is conducted at a temperature of 25° to 40° C.

11. The method as in claim 1, wherein step (1) is conducted for 20 to 60 seconds.

12. The method as in claim 1, wherein the staining solution further comprises a water soluble organic solvent.

13. The method as in claim 12, wherein the organic solvent is at least one selected from the group consisting of a lower alkanol, a lower alkylene glycol and a lower alkylene glycol monoloweralkyl ether.

14. The method as in claim 12, wherein the water soluble organic solvent is ethylene glycol.

15. A reagent for staining malaria infected cells which comprises:

at least one first dye of an Auramine analogue having the formula (I) as defined in claim 1, at least one second dye of condensed benzene derivatives having the formula (II) as defined in claim 1, and a water soluble organic solvent capable of dissolving the first and second dyes.

16. The reagent as in claim 15, wherein the first dye is Auramine O.

17. The reagent as in claim 15, wherein the second dye is 3,3'-di-lower alkyl-2,2'-oxacarbocyanine halide.

18. The reagent as in claim 15, wherein the second dye is 3,3'-diethyl-2,2'-oxacarbocyanine iodide.

19. The reagent as in claim 15, wherein the first and second dyes are contained at a concentration of 0.005 to 0.4 w/v % and 0.005 to 0.5 w/v %, respectively.

20. The reagent as in claim 15, wherein the organic solvent is at least one selected from the group consisting of a lower alkanol, a lower alkylene glycol and a lower alkylene glycol monoloweralkyl ether.

21. The reagent as in claim 15, wherein the organic solvent is ethylene glycol.

22. The method as in claim 1, wherein the test sample comprises human blood.

* * * * *